United States Patent
Case et al.

(10) Patent No.: US 7,905,826 B2
(45) Date of Patent: *Mar. 15, 2011

(54) METHODS FOR MODIFYING VASCULAR VESSEL WALLS

(75) Inventors: Brian C. Case, Bloomington, IN (US); Michael C. Hiles, Lafayette, IN (US); Jacob A. Flagle, Indianapolis, IN (US); F. Joseph Obermiller, West Lafayette, IN (US); Umesh H. Patel, West Lafayette, IN (US)

(73) Assignee: Cook Incorporated, Bloomington, IN (US)

( * ) Notice: Subject to any disclaimer, the term of this patent is extended or adjusted under 35 U.S.C. 154(b) by 1406 days.

This patent is subject to a terminal disclaimer.

(21) Appl. No.: 11/295,866

(22) Filed: Dec. 7, 2005

(65) Prior Publication Data

US 2007/0004961 A1 Jan. 4, 2007

Related U.S. Application Data

(63) Continuation-in-part of application No. 11/266,166, filed on Nov. 3, 2005, now Pat. No. 7,387,604.

(60) Provisional application No. 60/633,798, filed on Dec. 7, 2004, provisional application No. 60/624,775, filed on Nov. 3, 2004.

(51) Int. Cl.
*A61F 2/00* (2006.01)
*A61F 19/00* (2006.01)

(52) U.S. Cl. ........................... 600/37; 623/1.24
(58) Field of Classification Search .......... 600/29, 600/36–37; 128/897–899; 623/1.1, 1.24, 623/1.25, 1.27, 1.28, 1.38, 1.44–1.54; 424/93.1, 93.7

See application file for complete search history.

(56) References Cited

U.S. PATENT DOCUMENTS

| | | | |
|---|---|---|---|
| 4,218,782 A | 8/1980 | Rygg | |
| 4,902,508 A | 2/1990 | Badylak et al. | |
| 4,956,178 A | 9/1990 | Badylak et al. | |
| 5,156,613 A | 10/1992 | Sawyer | |
| 5,156,620 A | 10/1992 | Pigott | |
| 5,275,826 A * | 1/1994 | Badylak et al. | 424/551 |
| 5,411,552 A | 5/1995 | Andersen et al. | |
| 5,476,471 A * | 12/1995 | Shifrin et al. | 606/151 |
| 5,554,389 A | 9/1996 | Badylak et al. | |
| 5,607,465 A | 3/1997 | Camilli | |
| 5,711,969 A | 1/1998 | Patel et al. | |
| 5,855,601 A | 1/1999 | Bessler et al. | |
| 5,885,619 A | 3/1999 | Patel et al. | |
| 5,955,110 A | 9/1999 | Patel et al. | |
| 5,968,096 A | 10/1999 | Whitson et al. | |
| 5,993,844 A | 11/1999 | Abraham et al. | |
| 6,099,567 A | 8/2000 | Badylak et al. | |
| 6,110,201 A | 8/2000 | Quijano et al. | |

(Continued)

FOREIGN PATENT DOCUMENTS

WO    WO 95/22611    8/1995

(Continued)

*Primary Examiner* — John P Lacyk
(74) *Attorney, Agent, or Firm* — Woodard, Emhardt, Moriarty, McNett & Henry LLP

(57) ABSTRACT

This invention relates in one aspect to the treatment of a vascular vessel with a biomaterial. The biomaterial can be a remodelable material that strengthens and/or supports the vessel walls. Additionally the biomaterial can include a variety of naturally occurring or added bioactive agents and/or viable cellular populations.

49 Claims, 6 Drawing Sheets

U.S. PATENT DOCUMENTS

| | | | |
|---|---|---|---|
| 6,126,686 A | 10/2000 | Badylak et al. | |
| 6,168,614 B1 | 1/2001 | Andersen et al. | |
| 6,200,336 B1 | 3/2001 | Badylak et al. | |
| 6,206,931 B1 | 3/2001 | Cook et al. | |
| 6,287,334 B1 | 9/2001 | Moll et al. | |
| 6,299,637 B1 | 10/2001 | Shaolian et al. | |
| 6,444,229 B2 | 9/2002 | Voytik-Harbin et al. | |
| 6,485,723 B1 * | 11/2002 | Badylak et al. | 424/93.7 |
| 6,508,833 B2 | 1/2003 | Pavcnik et al. | |
| 6,527,800 B1 | 3/2003 | McGuckin, Jr. et al. | |
| 6,572,650 B1 * | 6/2003 | Abraham et al. | 623/1.38 |
| 6,582,462 B1 | 6/2003 | Andersen et al. | |
| 6,666,892 B2 | 12/2003 | Hiles et al. | |
| 6,695,878 B2 | 2/2004 | McGuckin, Jr. et al. | |
| 6,716,241 B2 | 4/2004 | Wilder et al. | |
| 6,752,828 B2 | 6/2004 | Thornton | |
| 7,387,604 B2 * | 6/2008 | Case et al. | 600/37 |
| 2001/0011187 A1 | 8/2001 | Pavcnik et al. | |
| 2001/0039450 A1 | 11/2001 | Pavcnik et al. | |
| 2002/0123800 A1 | 9/2002 | Taheri et al. | |
| 2002/0188348 A1 | 12/2002 | DiMatteo et al. | |
| 2003/0026787 A1 | 2/2003 | Fearnot et al. | |
| 2003/0036795 A1 | 2/2003 | Andersen et al. | |
| 2003/0130726 A1 | 7/2003 | Thorpe | |
| 2003/0191525 A1 | 10/2003 | Thornton | |
| 2003/0208261 A1 | 11/2003 | Thorpe et al. | |
| 2004/0015230 A1 | 1/2004 | Moll et al. | |
| 2004/0027557 A1 | 2/2004 | Caputo et al. | |
| 2004/0049262 A1 | 3/2004 | Obermiller et al. | |
| 2004/0193253 A1 | 9/2004 | Thorpe et al. | |
| 2005/0192235 A1 | 9/2005 | Hunter et al. | |
| 2005/0222649 A1 | 10/2005 | Capuano et al. | |

FOREIGN PATENT DOCUMENTS

| | | |
|---|---|---|
| WO | WO 96/24661 | 8/1996 |
| WO | WO 96/25179 | 8/1996 |
| WO | WO 00/32112 | 6/2000 |
| WO | WO 01/19285 | 3/2001 |
| WO | WO 03/002165 | 1/2003 |
| WO | WO 03/070124 | 8/2003 |

* cited by examiner

METHODS FOR MODIFYING VASCULAR VESSEL WALLS

REFERENCE TO RELATED APPLICATIONS

This application claims the benefit of priority of U.S. Provisional Patent Application Ser. No. 60/633,798 filed Dec. 7, 2004 which is incorporated herein by reference in its entirety. This application is also a continuation-in-part of U.S. patent application Ser. No. 11/266,166 filed Nov. 3, 2005, now U.S. Pat. No. 7,387,604 which claims the benefit of priority of U.S. Provisional Patent Application Ser. No. 60/624,775 filed Nov. 3, 2004, each of which is hereby incorporated herein in its entirety.

BACKGROUND OF THE INVENTION

In general, the present invention relates to methods of treating patients suffering from defects or diseases of the vascular system. More specifically, the present invention is directed to methods for modifying vascular vessel walls.

Vascular vessels, such as veins and arteries, are prone to a variety of cardiovascular disorders, for example, weakened walls possibly caused by arteriosclerosis or infection; and aneurysms, e.g. saccular, fusiform, and dissecting aneurysms. In the absence of treatment, the risks for further damage or rupture of an aneurysm can be very high and highly lethal should it occur. However, treatments for these defects may require surgical intervention, which also poses significant risks. For example, it is suggested that for certain aortic or venous aneurysms, that a portion of the vessel be resected and replaced with vascular graft, which is typically taken from one of the patient's extremities. Removal of a vein or artery from a patient's leg or arm can be quite painful for the patient even months after the initial surgery. Additionally, blood flow in that leg or arm is also compromised. A second surgical site also poses additional risks to infections and other complications. It has also been suggested to use a synthetic graft material repair the defect. Complications can also arise using synthetic materials to replace segments of vascular vessels, for example thrombosis, rejection or secondary infection are possible.

There is a continuing need for advancements in the relevant field, including improved and/or alternative treatment methods and devices. The present invention is addressed to these needs.

SUMMARY

In various aspects, the present invention relates to the treatment of patients with vascular diseases and the use of implantable devices therefor. While the actual nature of the invention covered herein can only be determined with reference to the claims appended hereto, certain forms and features, which are characteristic of the preferred embodiments disclosed herein, are described briefly as follows.

In one form, the present invention provides methods for modifying a vascular vessel that has a defect. The methods can include accessing a treatment site proximate to the defect; and introducing a remodelable biomaterial into the vessel wall or external of the vessel wall at the treatment site. For example such methods can include treating a vascular defect by reinforcing or remodeling the vessel wall. The vessel wall can be reinforced by partly or fully encircling the vessel with a cuff formed of the biomaterial. In certain embodiments the cuff is formed of a three dimensional construct of the biomaterial. In other embodiments, the cuff is formed from a fluidized form of the biomaterial, which has gelled or solidified either prior to or after implantation in the patient. The biomaterial can comprise a collagen-based material such as an extracellular matrix material. Submucosa tissue or another similar collagenous layer can be used. Additionally, the biomaterial can include added or retained bioactive agents and/or viable cells. The biomaterial can serve as a matrix to retain the bioactive agents and support a remodeling process. Other examples of treatment methods include implanting or introducing a biomaterial that can shrink in vivo. This propensity to shrink can be used to support and/or modify the vessel walls.

In another form, the present invention provides methods for treating a patient with a vascular defect. The method comprises introducing a delivery device through the patient's vasculature to a treatment site proximate to the defect; and delivering a remodelable biomaterial into or external of a wall of the vessel, or a combination thereof. In certain embodiments, the delivery device can be a needle or a cannulated delivery device. The delivery device can be introduced in to the patient's vascular, e.g., intra-lumenally (intravascularly), at a site either adjacent to or remote from the vascular defect. In other embodiments, the delivery device can be introduced exo-lumenally (exovascularly). The biomaterial can be an injectable composition containing a flowable mass of submocosa or other ECM derived material. The injectable biomaterial can be allowed or induced to gel or otherwise harden upon injection into the treatment site.

In another form the present invention provides methods for treating a vascular vessel in a patient. The method comprises introducing a remodelable biomaterial into or externally of a wall of the vessel in a region proximate to aneurysm or wall defect.

The method can include using a three dimensional construct of the biomaterial of a fluidized form of the biomaterial. In ether form, the biomaterial can include a variety of added or naturally occurring bioactive agents and viable cells.

Further objects, features, aspects, forms, advantages and benefits shall become apparent from the description and drawings contained herein.

DETAILED DESCRIPTION

For the purposes of promoting an understanding of the invention, certain treatment methods, prosthesis devices, and materials will be discussed. It will nevertheless be understood that no limitation of the scope of the invention is thereby intended. Any alterations and further modifications in the described materials, prostheses, and treatment methods, and any further applications of the principles of the invention as described herein, are contemplated as would normally occur to one skilled in the art to which the invent relates.

The present invention provides methods, devices, and materials for treating vascular vessels at sites associated with vascular valves, or at sites other than those associated with vascular valves. Vascular vessels, including veins and arteries, are prone to a variety of diseases and defects that affect the function, strength, and integrity of the vessels in regions associated with valves within the vessels, or in other regions. Weakened vascular vessel walls can, for example, be caused by arteriosclerosis or infection; and aneurysms, e.g. saccular, fusiform, and dissecting aneurysms. The treatment according to the present invention can include introducing a biomaterial into a treatment site located in tissue adjacent the vessel and/or in the vessel's walls. The biomaterial provides a benefit to the vascular vessels, for example to treat defects and diseases as described more fully herein. The materials and methods described herein are advantageous for treatment of disorders associated with venous valves, particularly those occurring within limbs such as legs. Further, the biomaterial can be a remodelable material and may include one or more bioactive substances derived from the source of the biomaterial and/or added to the biomaterial. The remodelable biomaterial can be angiogenic. The biomaterial can also be seeded with or contain viable cells.

Figure 1:
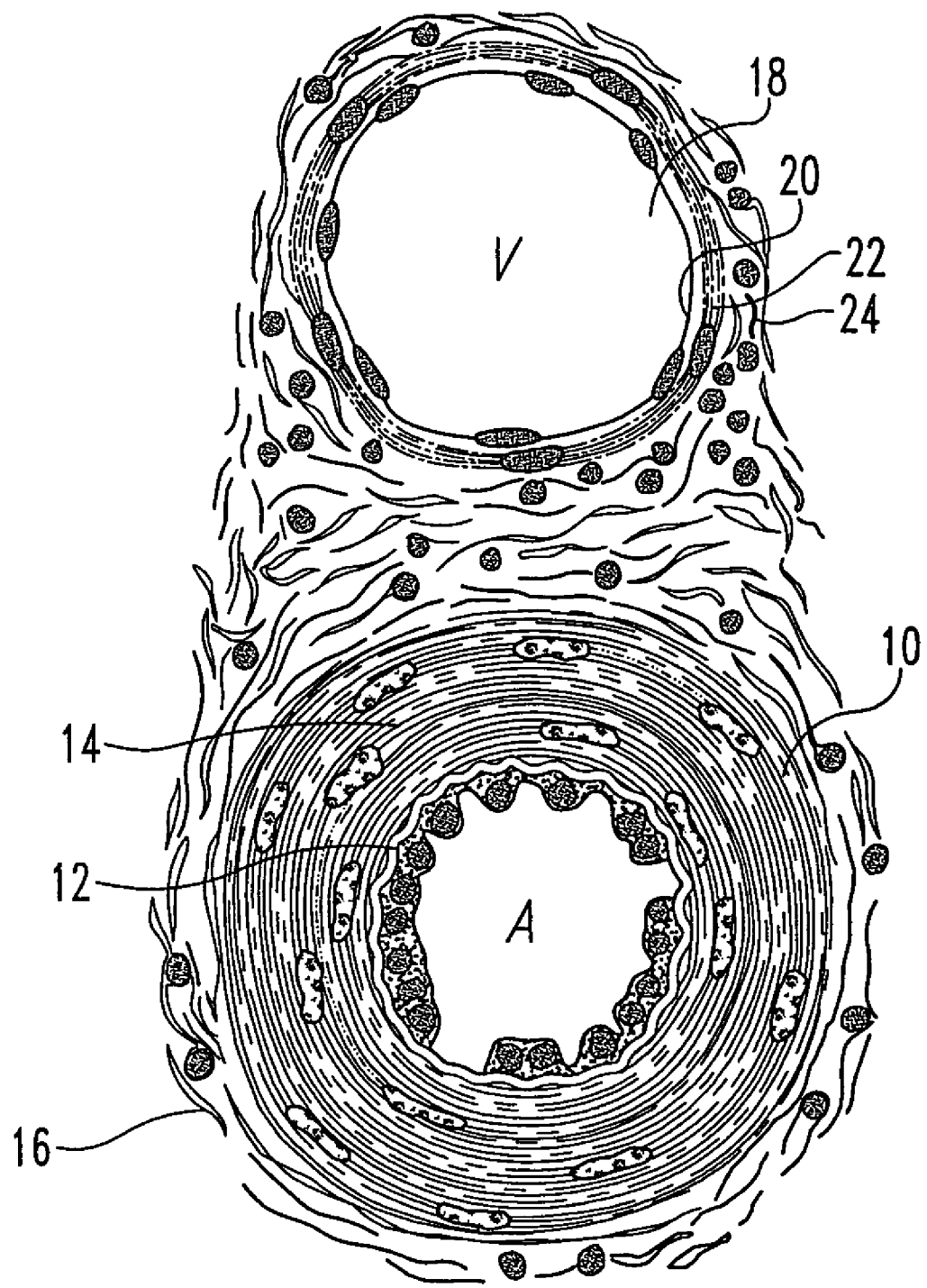
FIG. 1 provides illustrations of cross-sections of a vein and an artery.

For the purposes of certain aspects of the descriptions herein, FIG. 1 illustrates a cross-sectional view of a normal vein and an artery. Artery 10 is composed of three coats: an internal or endothelial coat (tunica intima) 12; a middle muscular coat (tunica media) 14, and an external connective tissue coating (tunica adventitia) 16. Typically, the two inner coats 12 and 14 together are very easily separated from the external coating. The vein 18 is also composed of three coats—internal, middle, and external coats 20, 22, and 24, respectively. A significant structural difference between veins and arteries is the comparative weakness of the middle coat of the vein. Because of this, the veins do not stand open when divided as the arteries do. Consequently, a vein tends to collapse without an internal fluid or fluid pressure, while a healthy artery substantially retains its natural shape and relative dimension regardless of whether or not it is conducting blood (or other fluid). Additionally, many veins, including the larger veins in the lower extremities, contain multiple valves to prevent the reflux or retrograde flow of blood away from the heart and thereby facilitate the return of blood to the heart.

"Remodeling" as used herein generally refers to the production of host tissue that replaces implanted material. The development of host tissue can occur at a functional rate about equal to the rate of biodegradation of the implanted material, resulting in a replacement of the implanted material by host-generated tissue, including for example structural proteins such as collagen, and cells.

In certain embodiments, the present invention provides a treatment for vascular vessels using a prosthesis formed of a biomaterial-containing construct. It is preferred to use a remodelable biomaterial that can also serve as a biocompatible scaffold with the ability to remodel host tissue. Accordingly, a naturally occurring biomaterial is highly desirable. In this regard, biomaterials for use in the present invention can be obtained as a purified collagen-containing matrix structure.

One such collagen-containing biomaterial is extracellular matrix (ECM). Preferred are naturally derived collagenous ECMs isolated from suitable animal or human tissue sources. Suitable extracellular matrix materials include, for instance, submucosa (including for example small intestinal submucosa, stomach submucosa, urinary bladder submucosa, or uterine submucosa, each of these isolated from juvenile or adult animals), renal capsule membrane, amnion, dura mater, pericardium, serosa, peritoneum or basement membrane materials, including liver basement membrane or epithelial basement membrane materials. These materials may be isolated and used as intact natural sheet forms, or reconstituted collagen layers including collagen derived from these materials and/or other collagenous materials may be used. For additional information as to submucosa materials useful in the present invention, and their isolation and treatment, reference can be made to U.S. Pat. Nos. 4,902,508, 5,554,389, 5,993,844, 6,206,931, and 6,099,567. Renal capsule membrane can also be obtained from warm-blooded vertebrates, as described more particularly in International Patent Application serial No. PCT/US02/20499 filed Jun. 28, 2002, published Jan. 9, 2003 as WO03002165.

The biomaterial can retain growth factors or other bioactive components native to a source tissue. For example, submucosa or other ECM materials may include one or more growth factors such as basic fibroblast growth factor (FGF-2), transforming growth factor beta (TGF-beta), epidermal growth factor (EGF), and/or platelet derived growth factor (PDGF). As well, submucosa or other ECM tissue used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

The biomaterial can be used alone, or in combination with one or more added pharmacologic agents, such as physiologically compatible minerals, growth factors (including vascular endothelial growth factors), antibiotics, chemotherapeutic agents, antigens, antibodies, genetic material, enzymes and hormones and the like.

In certain forms, the biomaterial of the invention can also be used in combination with other nutrients which support the growth of cells, e.g. eukaryotic cells such as endothelial (including non-keratinized or keratinized epithelial cells), fibroblastic cells, smooth muscle cells, cardiac muscle cells, multipotent progenitor or stem cells, pericytes, or any other suitable cell type (see, e.g. International Publication No. WO 96/24661 dated 15 Aug. 1996, publishing International Application No. PCT/US96/01842 filed 9 Feb. 1996). Such cells may optionally be included in the biomaterial construct or composition, for example being seeded upon or incorporated within the biomaterial construct or composition. The submucosa or other biomaterial substrate composition can be effective to support the proliferation and/or differentiation of mammalian cells, including human cells. Still further, the inventive methods herein may use a biomaterial that serves as a matrix that can support and produce genetically modified cells, (see, e.g., International Publication No. WO 96/25179 dated 22 Aug. 1996, publishing International Application No.

PCT/US96/02136 filed 16 Feb. 1996; and International Publication No. WO 95/22611 dated 24 Aug. 1995, publishing International Application No. PCT/US95/02251 filed 21 Feb. 1995). Such compositions for genetically modifying cells can include an ECM such as submucosa or another collagenous biomaterial as a three dimensional construct or a fluidized or flowable material in combination with a nucleic acid molecule containing a sequence to be expressed in cells, e.g. a recombinant vector such as a plasmid containing a nucleic acid sequence with which in vitro or in vivo target cells are to be genetically modified.

It some forms of practicing the invention, the biomaterial according to the present invention is substantially free of any antiviral agents or any antimicrobial-type agents, which can affect the biochemistry of the biomaterial and its efficacy upon implantation. One method of treating tissue material is to rinse the delaminated tissue in saline and soak it in an antimicrobial agent, for example, as disclosed in U.S. Pat. Nos. 4,956,178 and 6,666,892. While such techniques can optionally be practiced with isolated collagenous ECMs such as submucosa in the present invention, preferred embodiments avoid the use of antimicrobial agents and the like, which not only can affect the biochemistry of the collagenous biomaterial but also can be unnecessarily introduced into the tissues of the patient.

Irrespective of the origin of the biomaterial, a prosthesis for use in the present invention can be made thicker by making multilaminate constructs, for example SIS constructs or materials as described in U.S. Pat. Nos. 5,968,096; 5,955,110; 5,885,619; and 5,711,969; the disclosures of which are entirely and expressly incorporated by reference. The layers of the laminated construct can be bonded together via a crosslinking agent, a bonding agent, dehydrothermal bonding and/or by use of biotissue welding technique(s), or other suitable means.

In certain embodiments, the ECM or other biomaterial can be initially processed to provide a predetermined, three-dimensional shape or construct, which will be implanted into the patient as a prosthesis and will substantially retain its shape during remodeling or replacement of the graft with endogenous tissues. Illustratively, in embodiments wherein a sheet-form collagenous biomaterial is provided partially or completely encircling a vein or artery, the biomaterial can be processed to have the shape of a complete or partial cylinder configured to fit around and contact the external walls of the vessel about which the construct is to be received. Processing to provide such shapes can include configuring the ECM or other biomaterial to a desired shape while fully or partially hydrated, and dehydrating the material while in such shape. Such dehydrating may for example be conducted by air drying, lyophilization, vacuum pressing, or other suitable techniques.

For treatment of blood containing vessels in accordance with the present invention, and particularly for situations in which exposure of an amount of the biomaterial to the interior of the vessel is needed or a risk, the biomaterial can be treated to reduce any thrombogenic character that it may have. In this regard, an antithrombotic agent, such as, heparin or a heparin derivative may be bound to the biomaterial, construct or a prosthesis formed from the construct by any suitable method including physical, ionic, or covalent bonding. For example, this may be accomplished for example by applying solution of heparin or a heparin derivative to the biomaterial's surface or by dipping the biomaterial in the solution. In one embodiment, heparin is bound to the biomaterial using a suitable crosslinking agent such as a polyepoxide or carbodiimide cross linking agent such as 1-ethyl-3-(3-dimethylaminopropyl)-carbodiimide hydrochloride (EDC). In multi-layer constructs, heparin or other agents can be applied to the layers individually before incorporation of the layer into the construct, after the layers are incorporated into the construct (e.g. coating a luminal surface of an inner tubular layer), or both. Heparin can also be applied using a benzalkonium heparin (BA-Hep) isopropyl alcohol solution. This procedure treats the collagen with an ionically bound BA-Hep complex. Other coating, bonding, and attachment procedures, which are known in the art, can also be used. As well, in the case of flowable (e.g. injectable) biomaterials, heparin or one or more other anti-thrombogenic agents may be incorporated into the formulation utilized in soluble form and/or bound to any suspended particulate biomaterial within the formulation.

Figure 2:
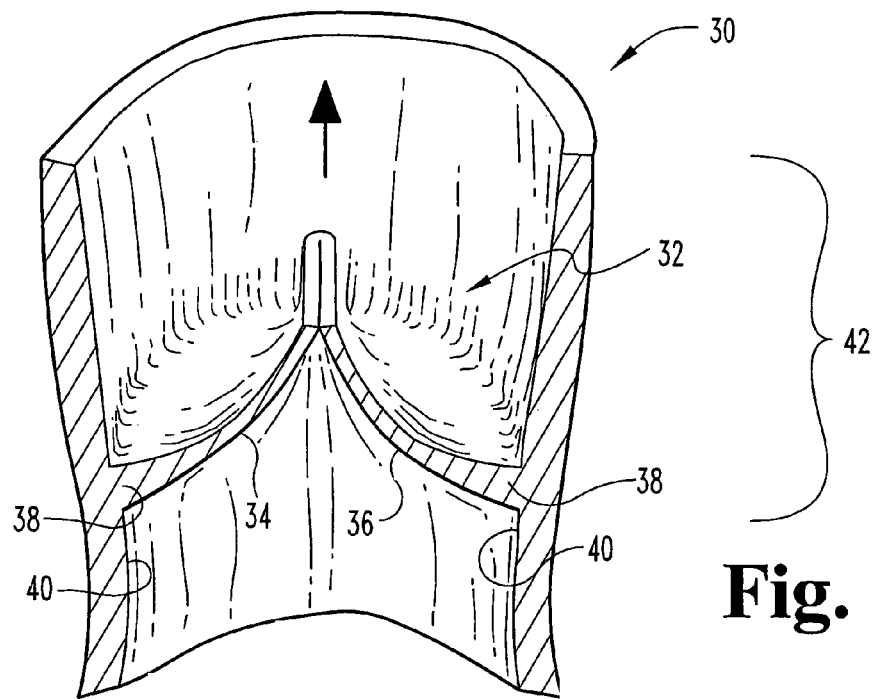
FIG. 2 is a cross-sectional view of a vascular vessel exhibiting one manifestation of a defect.

The present invention provides for the treatment of vascular defects associated with vascular valves, in certain of its embodiments. In preferred embodiments, the present invention provides for the treatment of vascular defects associated with venous valves. Illustratively, FIG. 2 shows a cross-sectional view of a portion of vascular vessel 30 having a defect generally depicted as distended wall 32. Typically, although not required, the distended wall is indicative of a weakened vascular wall. The weakened wall portion can present a serious risk of rupture that can lead to death and/or interruption of blood flow and function of a nearby valve.

In certain embodiments of the invention, such a diseased or defective region of the vascular vessel is identified in the patient and is accessed for treatment. This access can be provided, for example, using surgical cut-down procedures, or using minimally invasive procedures such as percutaneous and/or endoscopic techniques. Typically the defect (aneurysm, fistula or the like) is also identified/or confirmed and the treatment methods tailored accordingly. For treatment methods of the invention including the implantation of biomaterials external of the vascular vessel, exposure of or other access to the entire external circumference of the vascular vessel, or only to one or multiple points around the circumference of the vessel, or between two adjacent vessels, may be utilized.

In other treatment methods, which use a fluidized biomaterial, access to the treatment site can be accomplished by introducing a needle or other cannulated delivery device subcutaneously or intravascularly to deliver the biomaterial to the treatment site. When accessed intravascularly the delivery device can be guided through a portion of the patient's vascular system using known imaging techniques.

Figure 3:
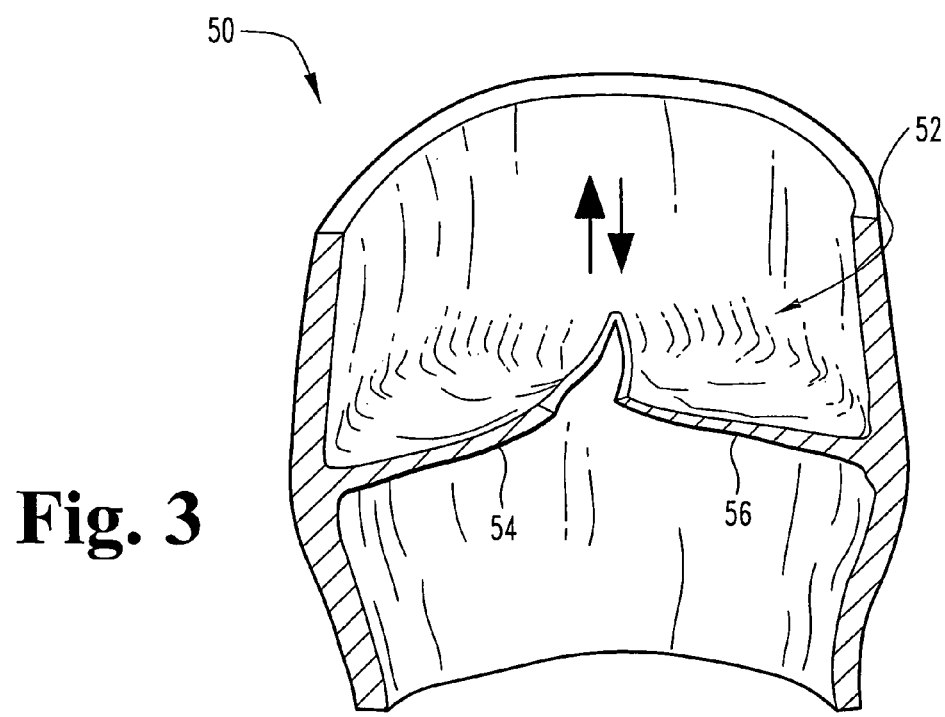
FIG. 3 is a cross-sectional view of a remodeled vascular vessel with a band of biomaterial external to the vessel wall in accordance with the present invention.

FIG. 3 is an illustration of a vascular vessel 50 and including a band 52 of biomaterial external to the vessel wall 54 resulting from one form of treatment according to one form of treatment according to the present invention. Band 52 of biomaterial can be used to address the defect or disorder in the vascular vessel. In one form, band 52 can provide support for the vessel wall 54 or cover a nick or tear in the vessel to name but two applications. Band 52 can be formed by wrapping a construct of the biomaterial about the outer surface of vessel 50, such as discussed below for FIGS. 4 and 6. Alternatively, band 52 can be formed by applying a fluidized biomaterial adjacent to the external surface of vessel 50 external connective coating of the vessel.

Figure 4:
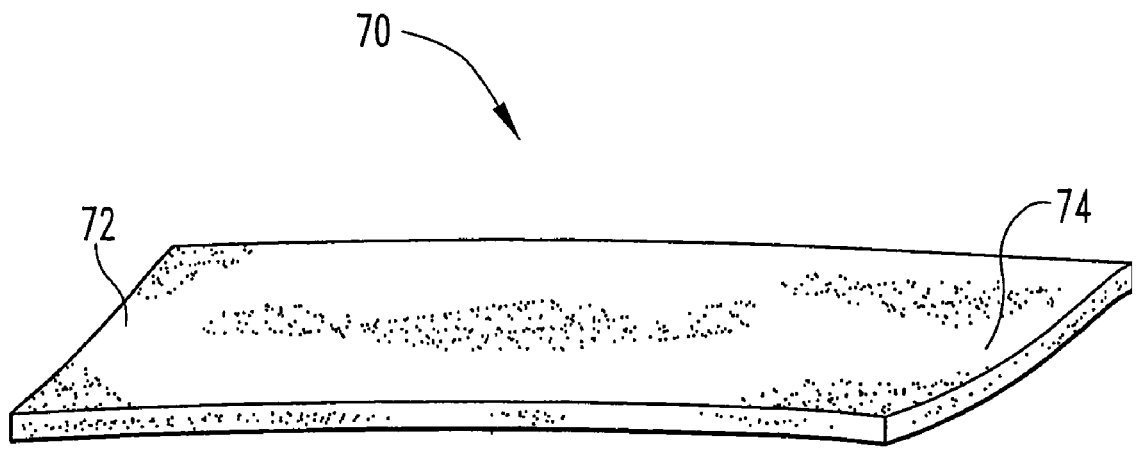
FIG. 4 is one embodiment of a construct formed of a sheet of a biomaterial in accordance with the present invention.

FIG. 4 is an illustration of one embodiment of a construct 70 to form a prosthesis in accordance with the present invention. Construct 70 is formed of a remodelable biomaterial, and in one particular embodiment construct 70 is formed from submucosa. Construct 70 is illustrated as an elongated, planar construct, preferably in the form of a flexible sheet. Construct 70 can be composed of a single layer or of several layers as a laminate of the remodelable biomaterial. Construct 70 can be sized and shaped either prior to or during surgery to approximate at least a portion of the external circumference of a targeted vessel. Further, construct 70 can be prepared to include one or more bioactive agents and/or cellular populations depending upon the desired treatment regime.

In use, once the treatment site has been accessed sufficiently, construct 70 is wrapped about the external circumference of the target vessel overlaying the treatment site. Construct 70 can partly or completely encircle the vessel. The first and second ends 72 and 74 of the construct 70 can be sutured or secured to the external circumference of the vessel wall in certain embodiments. In other embodiments, construct 70 is sized and formed such that the two opposite ends 72 and 74 touch or overlap each other. The two edges can be secured together using conventional means including suturing to each other (and/or to the vessel wall), tissue welding (see e.g. U.S. Pat. No. 5,156,613), and/or bonding agents such as fibrin glue, or other suitable techniques.

Figure 5:
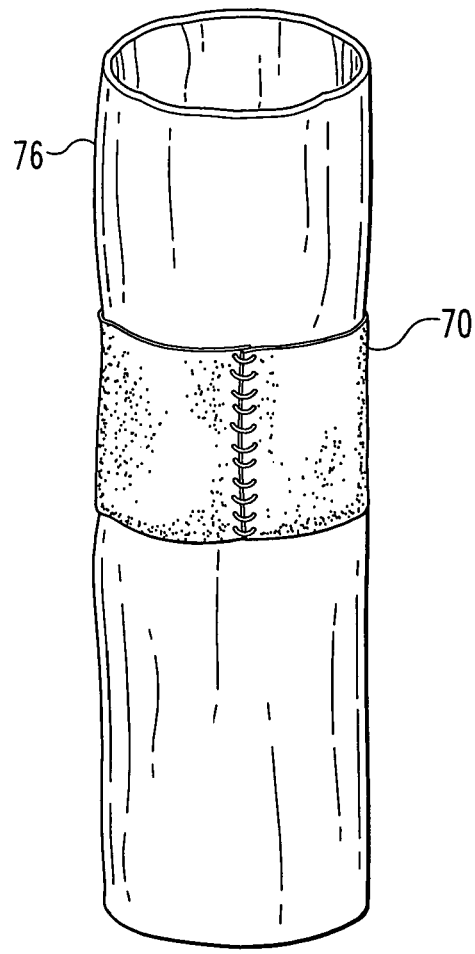
FIG. 5 illustrates the positioning of the prosthesis of FIG. 4 about a vessel in accordance with the present invention.

In this regard, FIG. 5 provides an illustration of construct 70 disposed about the external wall (or connective tissue coating) of a vessel 76. Construct 70 can be secured using sutures. The illustrated construct 70 can be used to remodel and/or support the vessel wall against initial or continued distention. Further, construct 70 can be used to reinforce or repair the vessel wall so that the vessel can withstand or exceed anticipated dynamic fluid pressure to which it may be subjected during a patient's normal level of physical activity.

Figure 6:
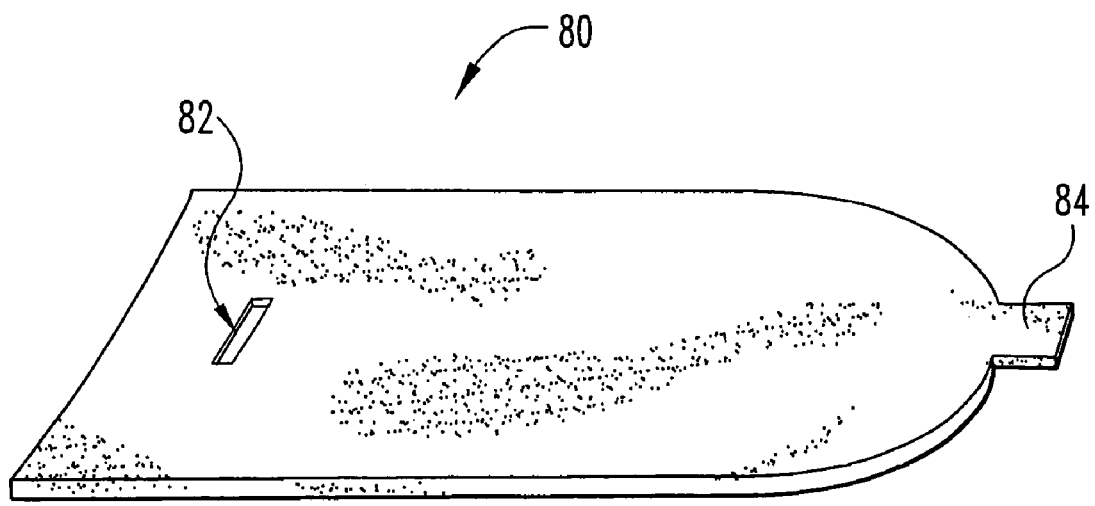
FIG. 6 is an illustration of an alternative embodiment of a construct formed of a sheet of a biomaterial in accordance with the present invention.

FIG. 6 illustrates an alternative embodiment of a construct 80 for use in the present invention. Construct 80 includes a slot 82 formed at its first end and a corresponding tab 84 extending from a second end. In use, tab 84 can be inserted into slot 82 to provide a generally circular cuff or band that can be placed around a vein or artery. Additionally, the ends, including tab 84, can optionally be secured together as discussed above for construct 70.

Figure 7:
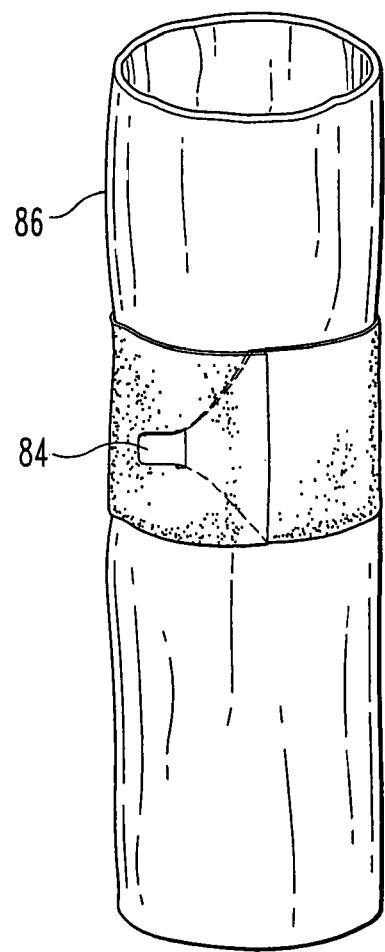
FIG. 7 illustrates the positioning of the prosthesis of FIG. 6 about a vessel in accordance with the present invention.

FIG. 7 provides an illustration of construct 80 received and secured around a vascular vessel 86 in the region of a treatment site. In particular, as with the construct 70 illustrated in FIG. 5, the illustrated construct 80 covers the area of the vein wall corresponding to the base of the leaflets. This positioning can be used to support the vein wall against initial or continued distention and/or to re-shape the vessel to increase the burst strength improve elasticity of the vessel. It will also be understood that construct 80 can include plurality of tabs and corresponding number of slots to facilitate securing the construct around a vein or other vascular vessel.

Although FIG. 5 and FIG. 7 show the constructs 70 and 80 positioned about the exterior circumference of the vessel proximate to the base of the leaflets, it will be understood that other regions may also be treated in accordance with the invention. The prosthesis can be positioned directly at or about the base of the leaflets or below the base of the leaflets, i.e., further from the heart. Alternatively, the prosthesis can be positioned above the base of the leaflets, i.e., closer to the heart. In other embodiments, two or more prostheses can be used, for example, one placed above and another placed below the base of the leaflets. In still other embodiments, the prosthesis can include a reinforcing clamp or clip received around the construct 70 or 80. The reinforcing clamp or clip can provide further support and compress against the external side walls of vessel.

The thickness of the construct(s) to form the prosthesis can be selected depending upon the tissue or biomaterial used, its intended use, and/or a prescribed treatment regime. In preferred embodiments for the treatment of veins and arteries, the biomaterial can be provided in a thickness of between about 50 and about 500 microns. It will be understood that the thickness of the construct/prosthesis can also be varied or, in particular, increased by laminating two or more layers of a biomaterial onto one another. It will also be understood that other configurations of the prosthesis such as the tissue constructs described in U.S. patent application Ser. No. 10/068,212 filed Feb. 6, 2002, can be used.

As discussed above, when the vessel exhibits a defect such as that described above for venous valvular dysfunction, the construct or prosthesis can serve to modify the shape of the vessel in the region of the leaflet bases and/or in regions immediately upstream or downstream of the leaflet bases. This, in turn, can reduce the interior dimension, in particular the interior diameter of the vessel.

A sufficient amount of the remodelable biomaterial is used to treat the vessel. In certain embodiments, a sufficient amount of material is used to encircle greater than about 20% of the circumference of the vessel; more preferably, a sufficient amount of the remodelable biomaterial is used to encircle greater than about 60% of the vessel; still more preferable, greater than about 80% of the vessel. In certain embodiments, an effective amount of the biomaterial is implanted about the vessel to reinforce the vessel wall, and/or to modify the diameter or shape of the vessel wall.

In some embodiments of the invention, the biomaterial is selected so as to retract or shrink after implantation in vivo. For instance, as a remodelable material retracts upon remodeling, it can press against or compress the periphery of the vessel. The remodelable material can be prepared to shrink at varying rates and to varying extents as desired. The shrinkage can also be controlled by a judicious selection of the source of the biomaterial and its preparation. For example the biomaterial can include a two or more layers, which are layers can be obtained from different tissue or obtained from the same tissue type but prepared differently. Alternatively or in addition, the selected biomaterial may exhibit anisotropic shrinkage, e.g. upon remodeling with host tissue. Consequently, the biomaterial shrinks to a greater extent in a first direction while exhibiting relatively less shrinkage in a second direction. Two or more layers of such a biomaterial either alone or in conjunction with other layers can be laminated such that the anisotropic shrinkage affects of the layers either complements each other, e.g. as in multilaminate materials having the layers oriented with their directions of maximal shrinkage generally aligned, or interferes with or modifies each other, e.g. as in multilaminate materials having the layers oriented with their directions of maximal shrinkage non-aligned or generally transverse to one another.

The biomaterial can also be crosslinked to vary and/or control the extent and/or rate of shrinkage. Increasing the amount (or number) of crosslinkages within the biomaterial or between two or more layers of the construct can be used to decrease the relative amount of shrinkage. However, crosslinkages within the biomaterial may also effect its remodelability. Consequently, in applications where tissue remodeling is desired, the biomaterial may substantially retain its native level of crosslinking, or the amount of added crosslinkages within the biomaterial can be judiciously selected depending upon the desired treatment regime. In many cases, the biomaterial will exhibit remodelable properties such that the remodeling process occurs over the course of several days or several weeks. In preferred embodiments, the remodeling process occurs within a matter of about 5 days to about 12 weeks.

For use in the present invention, introduced crosslinking of the biomaterial may be achieved by photo-crosslinking techniques, by chemical crosslinkers, or by protein crosslinking induced by dehydration or other means. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

When a laminate of material is used in the present invention, the layers of the laminate can be additionally crosslinked to bond multiple submucosa layers to one another. Thus, additional crosslinking may be added to individual submucosa layers prior to bonding to one another, during bonding to one another, and/or after bonding to one another.

In some embodiments of the invention, the prosthesis is prepared using a two component bonding agent such as fibrin glue (e.g., having thrombin and fibrinogen as separate components). To prepare such prostheses, subsequent layers are added after coating the previously-applied layer with a first component of the bonding agent (e.g., thrombin) and coating a layer to be applied with a second component of the bonding agent (e.g., fibrinogen). Thereafter, the layer to be applied is positioned over the previously-applied layer so as to bring the two bonding components into contact, thus causing the curing process to begin. This process can be repeated for any and all additional layers in a laminated construct. Additionally this process can be used to bond the ends of a prosthesis together in vivo.

In another mode of treatment, an injectable or otherwise flowable biocompatible material can be introduced in the patient to treat a vascular vessel site associated with a valve. For example, such a composition can be introduced into the vessel wall, e.g. into or in between one or more coatings of the vessel wall, and/or can be introduced into an external region surrounding a vessel wall, e.g. in contact with the external connective tissue coating (tunica adventitia) of an vein or artery. The injectable or flowable composition can be introduced at a single site or at a plurality of sites within the wall of a vascular vessel and/or about the external periphery of the vascular vessel. Relatively non-invasive modes of introduction will be advantageous, e.g. involving the delivery of the flowable composition through a cannulated device such as a needle or catheter.

In certain embodiments of the invention, an effective amount of a flowable composition is injected or otherwise introduced so as to provide support for and/or increase the strength of vessel walls. The introduced composition can include one or more bioactive agents or viable cellular populations, or combinations of these. Non-limiting examples of bioactive agents are listed above. Preferably the bioactive agents are effective to promote tissue growth.

While other biocompatible materials that can provide bulk mass to reinforce or modify the shape of the vessel walls may be used, the injectable or flowable composition for use in the invention desirably comprises an ECM composition. For example, fluidized submucosa can be prepared as described in U.S. Pat. Nos. 5,275,826 and 6,444,229. Fluidized or otherwise flowable ECM compositions may also be prepared as described in co-pending International Patent Application No. PCT/US04/27557 filed Aug. 25, 2004 and entitled Graft Materials Containing Bioactive Substances, and Methods for Their Manufacture. In this regard, the flowable compositions of the invention can be prepared from an isolated ECM material, for example one of those listed above. The ECM material is used to prepare a solubilized mixture including components of the material. This can be achieved by digestion of the ECM material in an acidic or basic medium and/or by contact with an appropriate enzyme or combination of enzymes.

The ECM material can be reduced to particulate form to aid in the digestion step. This can be achieved by tearing, cutting, grinding or shearing the isolated ECM material. Illustratively, shearing may be conducted in a fluid medium, and grinding may be conducted with the material in a frozen state. For example, the material can be contacted with liquid nitrogen to freeze it for purposes of facilitating grinding into powder form. Such techniques can involve freezing and pulverizing submucosa under liquid nitrogen in an industrial blender.

Any suitable enzyme may be used for an enzymatic digestion step. Such enzymes include for example serine proteases, aspartyl proteases, and matrix metalloproteases. The concentration of the enzyme can be adjusted based on the specific enzyme used, the amount of submucosa to be digested, the duration of the digestion, the temperature of the reaction, and the desired properties of the final product. In one embodiment about 0.1% to about 0.2% of enzyme (pepsin, for example) is used and the digestion is conducted under cooled conditions for a period of time sufficient to substantially digest the ECM material. The digestion can be conducted at any suitable temperature, with temperatures ranging from 4-37° C. being preferred. Likewise, any suitable duration of digestion can be used, such durations typically falling in the range of about 2-180 hours. The ratio of the concentration of ECM material (hydrated) to total enzyme usually ranges from about 25 to about 125 and more typically the ratio is about 50, and the digestion is conducted at 4° C. for 24-72 hours. When an enzyme is used to aid in the digestion, the digestion will be performed at a pH at which the enzyme is active and more advantageously at a pH at which the enzyme is optimally active. Illustratively, pepsin exhibits optimal activity at pH's in the range of about 2-4.

The enzymes or other disruptive agents used to solubilize the ECM material can be removed or inactivated before or during the gelling process so as not to compromise gel formation or subsequent gel stability. Also, any disruptive agent, particularly enzymes, that remains present and active during storage of the tissue will potentially change the composition and potentially the gelling characteristics of the solution. Enzymes, such as pepsin, can be inactivated with protease inhibitors, a shift to neutral pH, a drop in temperature below 0° C., heat inactivation or through the removal of the enzyme by fractionation. A combination of these methods can be utilized to stop digestion of the ECM material at a predetermined endpoint, for example the ECM material can be immediately frozen and later fractionated to limit digestion.

The ECM material is enzymatically digested for a sufficient time to produce a hydrolysate of ECM components. The ECM can be treated with one enzyme or with a mixture of enzymes to hydrolyze the structural components of the material and prepare a hydrolysate having multiple hydrolyzed components of reduced molecular weight. The length of digestion time is varied depending on the application, and the digestion can be extended to completely solubilize the ECM material. In some modes of operation, the ECM material will be treated sufficiently to partially solubilize the material to produce a digest composition comprising hydrolyzed ECM components and nonhydrolyzed ECM components. The digest composition can then optionally be further processed to remove at least some of the nonhydrolyzed components. For example, the nonhydrolyzed components can be separated from the hydrolyzed portions by centrifugation, filtration, or other separation techniques known in the art.

Preferred gel compositions of the present invention are prepared from enzymatically digested vertebrate ECM material that has been fractionated under acidic conditions, for example including pH ranging from about 2 to less than 7, especially to remove low molecular weight components. Typically, the ECM hydrolysate is fractionated by dialysis against a solution or other aqueous medium having an acidic pH, e.g. a pH ranging from about 2 to about 5, more desirably greater than 3 and less than 7. In addition to fractionating the hydrolysate under acidic conditions, the ECM hydrolysate is typically fractionated under conditions of low ionic strength with minimal concentrations of salts such as those usually found in standard buffers such as PBS (i.e. NaCl, KCl, $Na_2HPO_4$, or $KH_2PO_4$) that can pass through the dialysis membrane and into the hydrolysate. Such fractionation conditions work to reduce the ionic strength of the ECM hydrolysate and thereby provide enhanced gel forming characteristics.

The hydrolysate solution produced by enzymatic digestion of the ECM material has a characteristic ratio of protein to carbohydrate. The ratio of protein to carbohydrate in the hydrolysate is determined by the enzyme utilized in the digestion step and by the duration of the digestion. The ratio may be similar to or may be substantially different from the protein to carbohydrate ratio of the undigested ECM tissue. For example, digestion of vertebrate ECM material with a protease such as pepsin, followed by dialysis, will form a fractionated ECM hydrolysate having a lower protein to carbohydrate ratio relative to the original ECM material.

Flowable ECM compositions capable of forming shape retaining gels can be used in the present invention. Such ECM compositions can be prepared from ECM material that has been enzymatically digested and fractionated under acidic conditions to form an ECM hydrolysate that has a protein to carbohydrate ratio different than that of the original ECM material. Such fractionation can be achieved entirely or at least in part by dialysis. The molecular weight cut off of the ECM components to be included in the gellable material is selected based on the desired properties of the gel. Typically the molecular weight cutoff of the dialysis membrane (the molecular weight above which the membrane will prevent passage of molecules) is within in the range of about 2000 to about 10000 Dalton, and more preferably from about 3500 to about 5000 Dalton.

In certain forms of the gellable ECM composition, apart from the potential removal of undigested ECM components after the digestion step and any controlled fractionation to remove low molecular weight components as discussed above, the ECM hydrolysate is processed so as to avoid any substantial further physical separation of the ECM components. For example, when a more concentrated ECM hydrolysate material is desired, this can be accomplished by removing water from the system (e.g. by evaporation or lyophilization) as opposed to using conventional "salting out"/centrifugation techniques that would demonstrate significant selectivity in precipitating and isolating collagen, leaving behind amounts of other desired ECM components. Thus, in certain embodiments of the invention, solubilized ECM components of the ECM hydrolysate remain substantially unfractionated, or remain substantially unfractionated above a predetermined molecular weight cutoff such as that used in the dialysis membrane, e.g. above a given value in the range of about 2000 to 10000 Dalton, more preferably about 3500 to about 5000 Dalton.

Vertebrate ECM material can be stored frozen (e.g. at about −20 to about −80° C.) in either its solid, comminuted or enzymatically digested forms, or the material can be stored after being hydrolyzed and fractionated. The ECM material can be stored in solvents that maintain the collagen in its native form and solubility. For example, one suitable storage solvent is 0.01 M acetic acid, however other acids can be substituted, such as 0.01N HCl. In one form, the fractionated ECM hydrolysate can be dried (by lyophilization, for example) and stored in a dehydrated/lyophilized state. The dried form can be rehydrated to prepare a flowable ECM composition capable of forming a gel.

In accordance with one embodiment, the fractionated ECM hydrolysate or other flowable ECM composition will exhibit the capacity to gel upon adjusting the pH of a relatively more acidic aqueous medium containing it to about 5 to about 9, more preferably about 6.6 to about 8.0, and typically about 7.2 to about 7.8, thus inducing fibrillogenesis and matrix gel assembly. In one embodiment, the pH of the fractionated hydrolysate is adjusted by the addition of a buffer that does not leave a toxic residue, and has a physiological ion concentration and the capacity to hold physiological pH. Examples of suitable buffers include PBS, HEPES, and DMEM. Illustratively, the pH of the fractionated ECM hydrolysate can be raised by the addition of a buffered NaOH solution to 6.6 to 8.0, more preferably 7.2 to 7.8, to facilitate the formation of an ECM-containing gel. Any suitable concentration of NaOH solution can be used for these purposes, for example including about 0.05 M to about 0.5 M NaOH. In accordance with one embodiment, the ECM hydrolysate is mixed with a buffer and sufficient 0.25N NaOH is added to the mixture to achieve the desired pH.

The ionic strength of the ECM hydrolysate is believed to be important in maintaining the fibers of collagen in a state that allows for fibrillogenesis and matrix gel assembly upon neutralization of the hydrolysate. Accordingly, if needed, the salt concentration of the ECM hydrolysate material can be reduced prior to neutralization of the hydrolysate. The neutralized hydrolysate can be caused to gel at any suitable temperature, e.g. ranging from about 4° C. to about 40° C. The temperature will typically affect the gelling times, which may range from 5 to 120 minutes at the higher gellation temperatures and 1 to 8 hours at the lower gellation temperatures. Typically, the hydrolysate will be effective to self-gel at elevated temperatures, for example at about 37° C. In this regard, preferred neutralized ECM hydrolysates will be effective to gel in less than about ninety minutes at 37° C., for example approximately thirty to ninety minutes at 37° C.

Additional components can be added to the ECM hydrolysate composition before, during or after forming the gel. For example, proteins carbohydrates, growth factors, therapeutics, bioactive agents, nucleic acids, cells or pharmaceuticals can be added. In certain embodiments, such materials are added prior to formation of the gel. This may be accomplished for example by forming a dry mixture of a powdered ECM hydrolysate with the additional component(s), and then reconstituting and gelling the mixture, or by incorporating the additional component(s) into an aqueous, ungelled composition of the ECM hydrolysate before, during (e.g. with) or after addition of the neutralization agent. The additional component(s) can also be added to the formed ECM gel, e.g. by infusing or mixing the component(s) into the gel and/or coating them onto the gel.

In one embodiment of the invention, a particulate ECM material will be added to the ECM hydrolysate composition, which will then be incorporated in the formed gel. Such particulate ECM materials can be prepared by cutting, tearing, grinding or otherwise comminuting an ECM starting material. For example, a particulate ECM material having an average particle size of about 50 microns to about 500 microns may be included in the gellable ECM hydrolysate, more preferably about 100 microns to about 400 microns. The ECM particulate can be added in any suitable amount relative to the hydrolysate, with preferred ECM particulate to ECM hydrolysate weight ratios (based on dry solids) being about 0.1:1 to about 200:1, more preferably in the range of 1:1 to about 100:1. The inclusion of such ECM particulates in the ultimate gel can serve to provide additional material that can function to provide bioactivity to the gel (e.g. itself including FGF-2 and/or other growth factors or bioactive substances as discussed herein) and/or serve as scaffolding material for tissue ingrowth.

In certain embodiments, an ECM hydrolysate material to be used in the invention will exhibit an injectable character and also incorporate an ECM particulate material. In these embodiments, the ECM particulate material can be included at a size and in an amount that effectively retains an injectable character to the hydrolysate composition, for example by injection through a needle having a size in the range of 18 to 31 gauge (internal diameters of 0.047 inches to about 0.004 inches). In this fashion, non-invasive procedures for tissue augmentation will be provided, which in preferred cases will involve the injection of an ungelled ECM hydrolysate containing suspended ECM particles at a relatively lower (e.g. room) temperature, which will be promoted to form a gelled composition when injected into a patient and thereby brought to physiologic temperature (about 37° C.).

In certain embodiments, flowable ECM compositions to be used in the invention may be disinfected by contacting an aqueous medium including ECM hydrolysate components with an oxidizing disinfectant. This mode of disinfection provides an improved ability to recover a disinfected ECM hydrolysate that exhibits the capacity to form beneficial gels. In certain preparative methods, an aqueous medium containing ECM hydrolysate components can disinfected by providing a peroxy disinfectant in the aqueous medium. This can be advantageously achieved using dialysis to deliver the peroxy disinfectant into and/or to remove the peroxy disinfectant from the aqueous medium containing the hydrolysate. In certain dinsinfection techniques, an aqueous medium containing the ECM hydrolysate is dialyzed against an aqueous medium containing the peroxy disinfectant to deliver the disinfectant into contact with the ECM hydrolysate, and then is dialyzed against an appropriate aqueous medium (e.g. an acidic aqueous medium) to at least substantially remove the peroxy disinfectant from the ECM hydrolysate. During this dialysis step, the peroxy compound passes through the dialysis membrane and into the ECM hydrolysate, and contacts ECM components for a sufficient period of time to disinfect the ECM components of the hydrolysate. In this regard, typical contact times will range from about 0.5 hours to about 8 hours and more typically about 1 hour to about 4 hours. The period of contact will be sufficient to substantially disinfect the digest, including the removal of endotoxins and inactivation of virus material present. The removal of the peroxy disinfectant by dialysis may likewise be conducted over any suitable period of time, for example having a duration of about 4 to about 180 hours, more typically about 24 to about 96 hours. In general, the disinfection step will desirably result in a disinfected ECM hydrolysate composition having sufficiently low levels of endotoxins, viral burdens, and other contaminant materials to render it suitable for medical use. Endotoxin levels below about 2 endotoxin units (EUs) per gram (dry weight) are preferred, more preferably below about 1 EU per gram, as are virus levels below 100 plaque forming units per gram (dry weight), more preferably below 1 plaque forming unit per gram.

The aqueous ECM hydrolysate composition can be a substantially homogeneous solution during the dialysis step for delivering the oxidizing disinfectant to the hydrolysate composition and/or during the dialysis step for removing the oxidizing disinfectant from the hydrolysate composition. Alternatively, the aqueous hydrolysate composition can include suspended ECM hydrolysate particles, optionally in combination with some dissolved ECM hydrolysate components, during either or both of the oxidizing disinfectant delivery and removal steps. Dialysis processes in which at least some of the ECM hydrolysate components are dissolved during the disinfectant delivery and/or removal steps are preferred and those in which substantially all of the ECM hydrolysate components are dissolved are more preferred.

The disinfection step can be conducted at any suitable temperature, and will typically be conducted between 0° C. and 37° C., more typically between about 4° C. and about 15° C. During this step, the concentration of the ECM hydrolysate solids in the aqueous medium can be in the range of about 2 mg/ml to about 200 mg/ml, and may vary somewhat through the course of the dialysis due to the migration of water through the membrane. In certain embodiments, a relatively unconcentrated digest is used, having a starting ECM solids level of about 5 mg/ml to about 15 mg/ml. In other embodiments, a relatively concentrated ECM hydrolysate is used at the start of the disinfection step, for example having a concentration of at least about 20 mg/ml and up to about 200 mg/ml, more preferably at least about 100 mg/ml and up to about 200 mg/ml. It has been found that the use of concentrated ECM hydrolysates during this disinfection processing results in an ultimate gel composition having higher gel strength than that obtained using similar processing with a lower concentration ECM hydrolysate. Accordingly, processes which involve the removal of amounts of water from the ECM hydrolysate resulting from the digestion prior to the disinfection processing step are preferred. For example, such processes may include removing only a portion of the water (e.g. about 10% to about 98% by weight of the water present) prior to the dialysis/disinfection step, or may include rendering the digest to a solid by drying the material by lyophilization or otherwise, reconstituting the dried material in an aqueous medium, and then treating that aqueous medium with the dialysis/disinfection step.

In one mode of operation, the disinfection of the aqueous medium containing the ECM hydrolysate can include adding the peroxy compound or other oxidizing disinfectant directly to the ECM hydrolysate, for example being included in an aqueous medium used to reconstitute a dried ECM hydrolysate or being added directly to an aqueous ECM hydrolysate composition. The disinfectant can then be allowed to contact the ECM hydrolysate for a sufficient period of time under suitable conditions (e.g. as described above) to disinfect the hydrolysate, and then removed from contact with the hydrolysate. In one embodiment, the oxidizing disinfectant can then be removed using a dialysis procedure as discussed above. In other embodiments, the disinfectant can be partially or completely removed using other techniques such as chromatographic or ion exchange techniques, or can be partially or completely decomposed to physiologically acceptable components. For example, when using an oxidizing disinfectant containing hydrogen peroxide (e.g. hydrogen peroxide alone or a peracid such as peracetic acid), hydrogen peroxide can be allowed or caused to decompose to water and oxygen, for example in some embodiments including the use of agents that promote the decomposition such as thermal energy or ionizing radiation, e.g. ultraviolet radiation.

In another mode of operation, the oxidizing disinfectant can be delivered into the aqueous medium containing the ECM hydrolysate by dialysis and processed sufficiently to disinfect the hydrolysate (e.g. as described above), and then removed using other techniques such as chromatographic or ion exchange techniques in whole or in part, or allowed or caused to decompose in whole or in part as discussed immediately above.

Peroxygen compounds that may be used in the disinfection step include, for example, hydrogen peroxide, organic peroxy compounds, and preferably peracids. Such disinfecting agents are used in a liquid medium, preferably a solution, having a pH of about 1.5 to about 10.0, more desirably about 2.0 to about 6.0. As to peracid compounds that can be used, these include peracetic acid, perpropioic acid, or perbenzoic acid. Peracetic acid is the most preferred disinfecting agent for purposes of the present invention.

When used, peracetic acid is desirably diluted into about a 2% to about 50% by volume of alcohol solution, preferably ethanol. The concentration of the peracetic acid may range, for instance, from about 0.05% by volume to about 1.0% by volume. Most preferably, the concentration of the peracetic acid is from about 0.1% to about 0.3% by volume. When hydrogen peroxide is used, the concentration can range from about 0.05% to about 30% by volume. More desirably the hydrogen peroxide concentration is from about 1% to about 10% by volume, and most preferably from about 2% to about 5% by volume. The solution may or may not be buffered to a pH from about 5 to about 9, with more preferred pH's being from about 6 to about 7.5. These concentrations of hydrogen peroxide can be diluted in water or in an aqueous solution of about 2% to about 50% by volume of alcohol, most preferably ethanol. Additional information concerning preferred peroxy disinfecting agents can be found in discussions in U.S. Pat. No. 6,206,931, which is herein incorporated by reference.

Flowable ECM materials of the present invention can be prepared to have desirable properties for handling and use. For example, fluidized ECM hydrolysates can be prepared in an aqueous medium, which can thereafter be effective to form of a gel. Such prepared aqueous mediums can have any suitable level of ECM hydrolysate therein. Typically, the ECM hydrolysate will be present in the aqueous medium at a concentration of about 2 mg/ml to about 200 mg/ml, more typically about 20 mg/ml to about 200 mg/ml, and in some embodiments about 30 mg/ml to about 120 mg/ml. In preferred forms, the aqueous ECM hydrolysate composition will have an injectable character, for example by injection through a needle having a size in the range of 18 to 31 gauge (internal diameters of about 0.047 inches to about 0.004 inches).

Furthermore, flowable ECM compositions can be prepared so that in addition to neutralization, heating to physiologic temperatures (such as 37° C.) will substantially reduce the gelling time of the material. It is contemplated that commercial products or systems of the invention and for practice of treatments of the invention may include (i) packaged, sterile powders which can be reconstituted in an acidic medium to form a flowable ECM composition, e.g. one which gels when neutralized and potentially heated; (ii) packaged, sterile aqueous compositions including solubilized ECM hydrolysate components under non-gelling (e.g. acidic) conditions; or (iii) packaged, sterile ECM gel compositions.

In certain embodiments, a medical kit for performing a treatment of a vascular vessel in accordance with the invention is provided that includes a packaged, sterile aqueous composition including solubilized ECM hydrolysate components under non-gelling (e.g. acidic) conditions, and a separately packaged, sterile aqueous neutralizing composition (e.g. containing a buffer and/or base) that is adapted to neutralize the ECM hydrolysate for the formation of a gel. In another embodiment, a medical kit for treatments of the invention includes a packaged, sterile, dried (e.g. lyophilized) ECM hydrolysate powder, a separately packaged, sterile aqueous acidic reconstituting medium, and a separately packaged sterile, aqueous neutralizing medium. In use, the ECM hydrolysate powder can be reconstituted with the reconstituting medium to form a non-gelled mixture, which can then be neutralized with the neutralizing medium. The thus neutralized flowable ECM material can then be delivered to a treatment site in accordance with the invention before or after it gels.

Medical kits as described above may also include a device, such as a syringe, for delivering the neutralized ECM hydrolysate medium to a patient. In this regard, the sterile, aqueous ECM hydrolysate medium or the sterile ECM hydrolysate powder of such kits can be provided packaged in a syringe or other delivery instrument. In addition, the sterile reconstituting and/or neutralizing medium can be packaged in a syringe, and means provided for delivering the contents of the syringe into a mixing container or another syringe containing the aqueous ECM hydrolysate medium or the ECM hydrolysate powder for mixing purposes. In still other forms of the invention, a self-gelling aqueous ECM hydrolysate composition can be packaged in a container (e.g. a syringe) and stable against gel formation during storage. For example, gel formation of such products can be dependent upon physical conditions such as temperature or contact with local milieu present at an implantation site in a patient. Illustratively, an aqueous ECM hydrolysate composition that does not gel or gels only very slowly at temperatures below physiologic temperature (about 37° C.) can be packaged in a syringe or other container and potentially cooled (including, for example frozen) prior to use for injection or other implantation into a patient for a treatment in accordance with the invention.

In particular applications, ECM hydrolysate compositions that form hydrogels at or near physiologic pH and temperature will be preferred for in vivo bulking applications, for example in the treatment of stress urinary incontinence, gastroesophageal reflux disease, cosmetic surgery, vesico urethral reflux, anal incontinence and vocal cord repair. These forms of the submucosa or other ECM gel have, in addition to collagen, complex extracellular matrix sugars and varying amounts of growth factors in other bioactive agents that can serve to remodel tissue at the site of implantation. These ECM hydrolysate compositions can, for example, be injected into a patient for these applications.

ECM gels and dry sponge form materials of the invention prepared by drying ECM gels can be used, for example, in wound healing and/or tissue reconstructive applications, or in the culture of cells.

The manipulations used to prepare ECM hydrolysate compositions and gellable or gelled forms thereof can also have a significant impact upon growth factors or other ECM components that may contribute to bioactivity. Techniques for modulating and sampling for levels of FGF-2, other growth factors, and/or bioactive substances can be used in conjunction with the manufacture of the described ECM hydrolysate compositions. Illustratively, the dialysis/disinfection processes described above employing peroxy compounds typically cause a reduction in the level of FGF-2 in the ECM hydrolysate material. In work to date as described in Examples 1-4, such processing using peracetic acid as disinfectant has caused a reduction in the level of FGF-2 in the range of about 30% to about 50%. Accordingly, to retain higher levels of FGF-2, one can process for a minimal about of time necessary to achieve the desired disinfection of the material; on the other hand, to reduce the FGF-2 to lower levels, the disinfection processing can be continued for a longer period of time.

In certain methods of manufacturing a flowable ECM composition, the disinfection process and subsequent steps will be sufficiently conducted to result in a medically sterile aqueous ECM hydrolysate composition, which can be packaged using sterile filling operations. In other manufacturing methods, any terminal sterilization applied to the ECM hydrolysate material (e.g. in dried powder, dry sponge form, non-gelled aqueous medium, or gelled form) can also be selected and controlled to optimize the level of FGF-2 or other bioactive substances in the product. Terminal sterilization methods may include, for example, high or low temperature ethylene oxide, radiation such as E-beam, gas plasma (e.g. Sterrad), or hydrogen peroxide vapor processing.

Preferred, packaged, sterilized ECM hydrolysate products for use in accordance with the invention will have an FGF-2 level (this FGF-2 being provided by the ECM hydrolysate) of about 100 ng/g to about 5000 ng/g based upon the dry weight of the ECM hydrolysate. More preferably, this value will be about 300 ng/g to about 4000 ng/g. As will be understood, such FGF-2 levels can be determined using standard ELISA tests (e.g. using the Quantikine Human Basic Fibroblast Growth Factor ELISA kit commercially available from R&D Systems).

Figure 8:
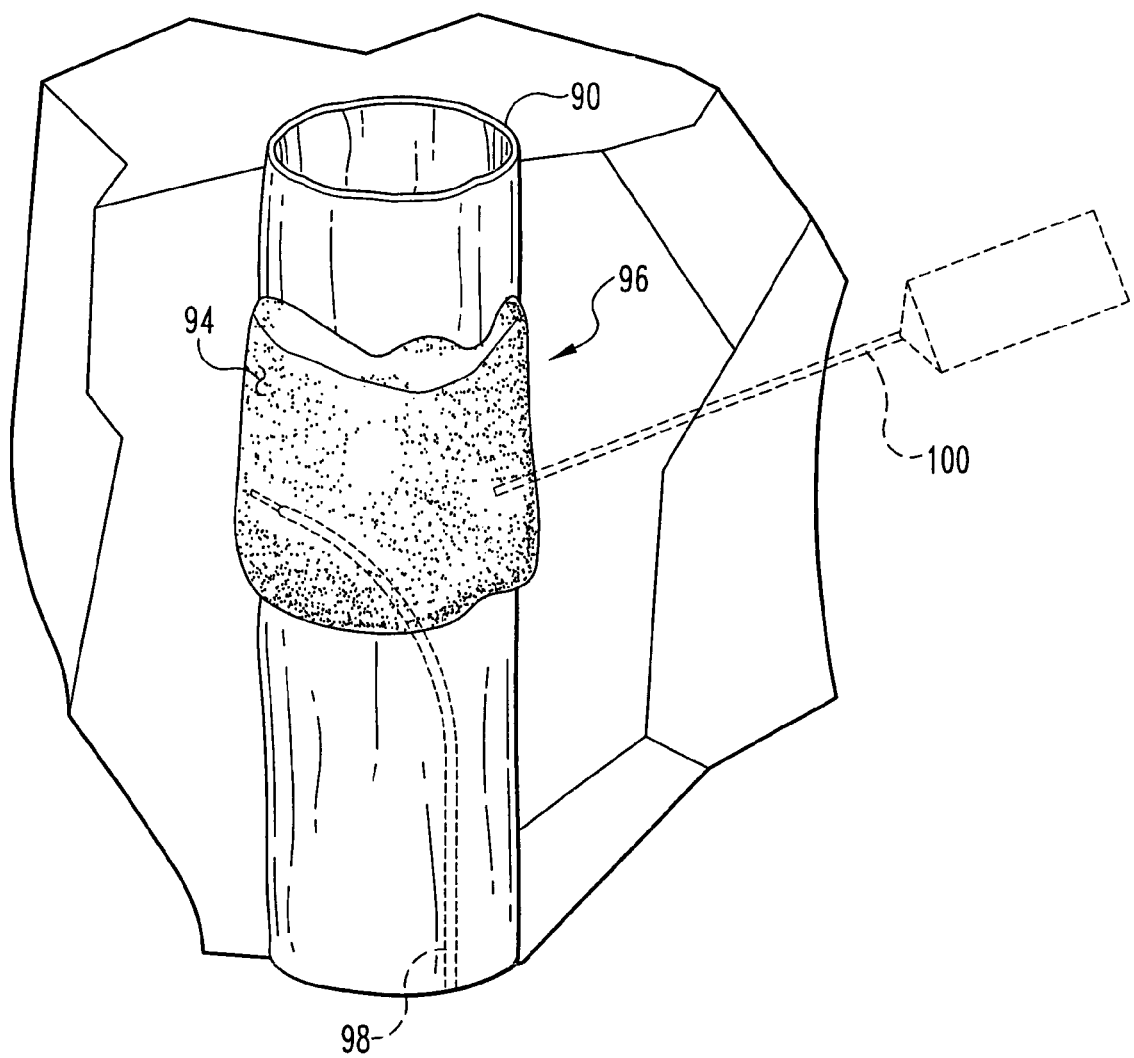
FIG. 8 provides an illustration of a tissue volume containing a vascular vessel and in which an injected mass of biomaterial forms a cuff around the vessel.
Figure 9:
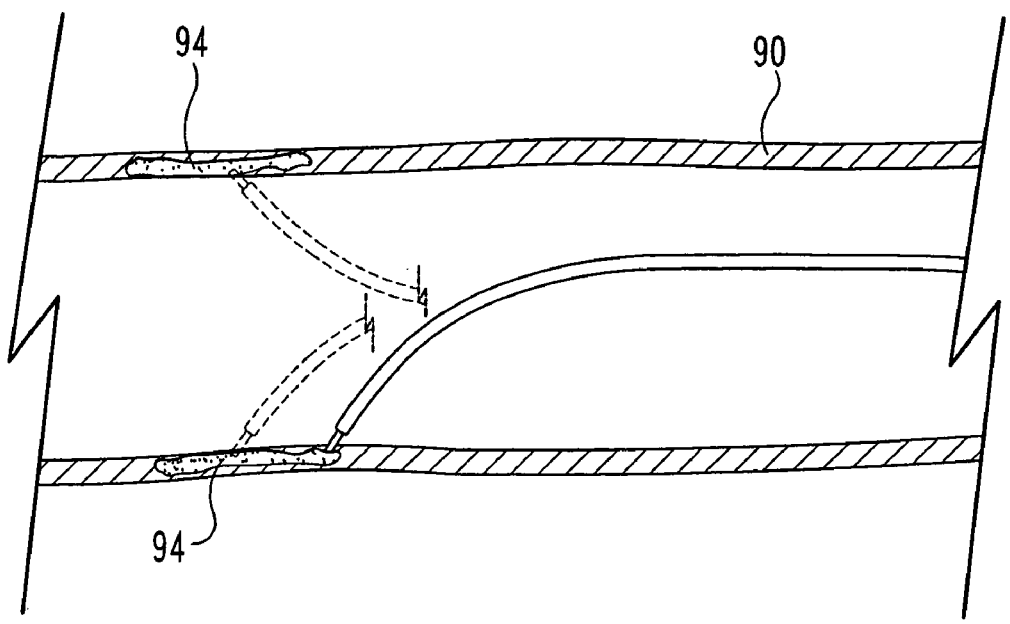
FIG. 9 provides a cross-sectional view illustrating the injection of a mass of material to surround a vessel in the region of a defect.

With reference now to FIGS. 8 and 9, in one illustrative embodiment of the invention, all or a portion of a vessel 90 in the region of a defect is surrounded by a flowable composition 94. Flowable composition 94 is desirably one that promotes the growth of tissue in the patient, and is desirably a flowable tissue graft material such as a flowable ECM composition. In certain embodiments, the flowable composition is injected about the periphery of the vessel, and allowed or caused to gel or otherwise harden to provide a cuff 96 of material suitable to supplement or support the vessel wall. Still further, in some embodiments of the invention, the cuff 96 can exhibit retraction or contraction upon ingrowth of patient tissue, so as to modify the shape of the vessel in the cuffed region, e.g. to reduce the internal diameter of the vessel. In addition or in the alternative, retraction or contraction of cuff 96 can increase burst strength and/or elasticity to the vessel wall. In certain embodiments, the flowable material is introduced by injection using a cannulated percutaneous device 98 such as one having needle, which is used to puncture and exit the vessel 90 at one or more sites and upon doing so is used to deliver the flowable composition through the cannula to surround all or a portion of the exterior of the vessel 90. Alternatively or in addition, an externally delivered needle 100 can be used to deliver the flowable composition to the exterior periphery of the vessel 90. The flowable mass, which optionally gels or otherwise hardens on its own or can be induced to gel or harden, can serve to reinforce the walls of the vessel 90 and/or to apply pressure to and re-shape the walls of the vessel. In certain embodiments, the flowable mass can be a remodelable ECM biomaterial or another material that promotes tissue ingrowth. In still further embodiments, such tissue ingrowth can lead to retraction or shrinkage of the introduced mass as it is replaced by host tissue, thus serving to promote close contact of the ingrown tissue with the vein wall and/or to re-shape the vein wall and potentially modify the function of the interior valve 92.

Figure 10:
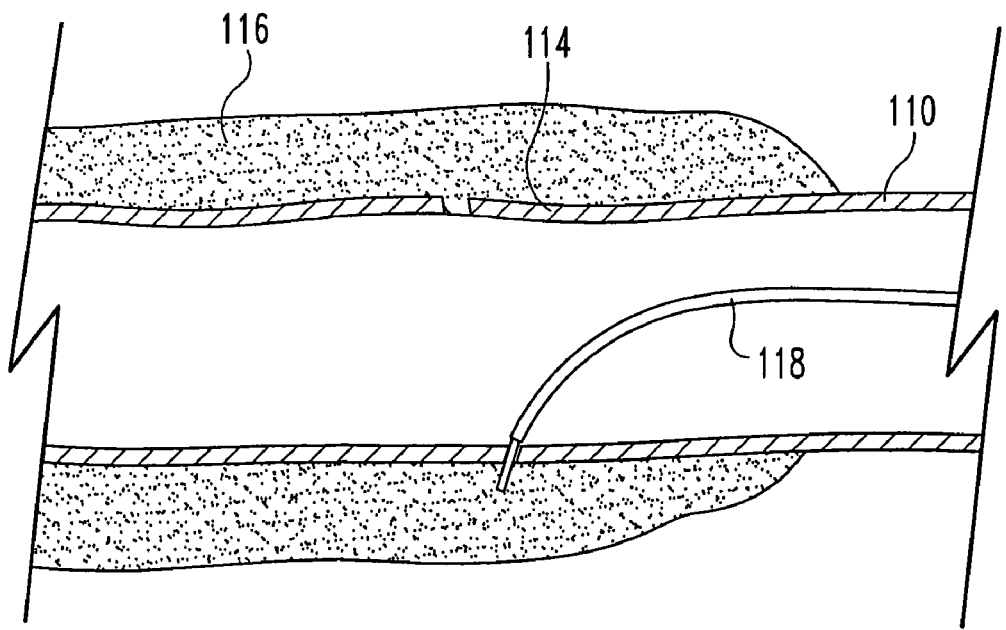
FIG. 10 provides a cross-sectional view illustrating the injection of a material into the vessel wall in the region of a defect.

FIG. 10 provides an illustration of a vessel 110 and wall portion 114 into which a therapeutic composition 116 has been introduced. Composition 116, may, for example, be effective to promote tissue growth, and may be a flowable biomaterial as discussed herein. Composition 116 can be delivered through a percutaneous needle device 118, which can be manipulated to one or multiple positions (see phantom) to deliver composition 116 into the vessel walls 114. Composition 116 and potential tissue development stimulated by composition 116 can serve to strengthen vessel walls 114, for example to protect against initial or continued distension. In addition or alternatively, localized retraction of vessel walls 114 stimulated by the introduction of composition 116 can serve to re-shape the vessel walls, for example to impact and improve upon the elasticity and reduce the risks to aneurysm rupture.

The prosthesis and biomaterial either as a construct or as a fluidized or flowable substance can optionally be rendered radiopaque in whole or in part by a variety of methods as discussed in WO 00/32112, which is incorporated herein. In one embodiment for the invention, when the biomaterial is formed into sheets whether in lyophilized or non-lyophilized form a radiopaque substance including but not limited to, tantalum such as tantalum powder, can be spread along the surface of the layers. When the prosthesis or biomaterial is provided as a flowable composition, the radiopaque substance can be combined either with the powdered form or as the hydrated/rehydrated form prior to or during treatment. Other radiopaque agents for use in this invention include bismuth, iodine, and barium as well as other conventional markers. It will be understood that the radiopaque substance may be incorporated homogeneously or inhomogeneously within or on the biomaterial to be implanted.

Embodiments of the invention have been discussed above generally in connection with treating vascular vessels at regions associated with defects. In other embodiments, the inventive methods, constructs and materials as described above can be used in the strengthening and/or reinforcement of vascular vessel walls in regions proximate to an introduced framed or frameless artificial vascular valve. As well, such strengthening or reinforcement techniques can be used in conjunction with other cut-down surgical or percutaneous treatments to improve an existing native valve, for example by manipulating or modifying the valve leaflets themselves. Certain embodiments of the invention, accordingly, involve patient treatment regimens which include treating a native valve or implanting an artificial valve in a vascular vessel in combination with strengthening or reinforcing walls of the vessel in affected or potentially affected regions associated with the treated or implanted valve. In more preferred embodiments, the vascular vessel is a vein, and the valve is a venous valve. In especially preferred aspects, veins within the legs or feet will be treated in accordance with the invention.

The invention also encompasses medical products for use in treatments of the invention, which products include a prosthesis device or flowable biocompatible material sealed within sterile medical packaging. The final, packaged product is provided in a sterile condition. This may be achieved, for example, by gamma, e-beam or other irradiation techniques, ethylene oxide gas, or any other suitable sterilization technique, and the materials and other properties of the medical packaging will be selected accordingly.

In order to promote a further understanding of the present invention and its features and advantages, the following specific examples are provided. It will be understood that these examples are illustrative and are not limiting of the invention.

Example 1

Raw (isolated/washed but non-disinfected) porcine small intestine submucosa was frozen, cut into pieces, and cryoground to powder with liquid nitrogen. 50 g of the submucosa powder was mixed with one liter of a digestion solution containing 1 g of pepsin and 0.5 M acetic acid. The digestion process was allowed to continue for 48-72 hours under constant stirring at 4° C. At the end of the process, the digest was centrifuged to remove undigested material. The acetic acid was then removed by dialysis against 0.01 M HCl for approximately 96 hours at 4° C. The resulting digest was transferred (without concentration) into a semipermeable membrane with a molecular weight cut off of 3500, and dialyzed for two hours against a 0.2 percent by volume peracetic acid in a 5 percent by volume aqueous ethanol solution at 4° C. This step served both to disinfect the submucosa digest and to fractionate the digest to remove components with molecular weights below 3500. The PAA-treated digest was then dialysed against 0.01 M HCl for 48 hours at 4° C. to remove the peracetic acid. The sterilized digest was concentrated by lyophilization, forming a material that was reconstituted at about 30 mg/ml solids in 0.01 M HCl. This material was neutralized with phosphate buffered NaOH to a pH of about 7.5-7.6 which provided a flowable material which formed a gel when heated to physiologic temperature.

Example 2

A second acetic acid processed submucosa gel was made using a process similar to that described in Example 1 above, except concentrating the digest prior to the PAA treatment. Specifically, immediately following the removal of acetic acid by dialysis, the digest was lyophilized to dryness. A concentrated paste of the digest was made by dissolving a pre-weighed amount of the lyophilized product in a known amount of 0.01 M HCl to prepare a mixture having an ECM solids concentration of about 50 mg/ml. The concentrated paste was then dialysed against the PAA solution for 2 hours and then against 0.01 M HCl for removal of PAA in the same manner described in Example 1. The digest was adjusted to about 30 mg/ml solids and neutralized with phosphate buffered NaOH to a pH of about 7.5-7.6, which upon heating to physiologic temperature formed a gel.

Example 3

An HCl processed submucosa gel was made using a procedure similar to that described in Example 1, except using 0.01 M of HCl in the pepsin/digestion solution rather than the 0.5 M of acetic acid, and omitting the step involving removal of acetic acid since none was present. The digest was used to form a gel as described in Example 1.

Example 4

Another HCl processed submucosa gel was made using a procedure similar to that described in Example 2, except using 0.01 M of HCl in the pepsin/digestion solution rather than the 0.5 M of acetic acid, and omitting the step involving removal of acetic acid since none was present. The digest was used to form a gel as described in Example 2.

The present invention contemplates other modifications as would occur to those skilled in the art. It is also contemplated that methodologies embodied in the present invention can be altered or added to other processes as would occur to those skilled in the art without departing from the spirit of the present invention. All publications, patents, and patent applications cited in this specification are herein incorporated by reference as if each individual publication, patent, or patent application was specifically and individually indicated to be incorporated by reference and set forth in its entirety herein.

Further, any theory of operation, proof, or finding stated herein is meant to further enhance understanding of the present invention and is not intended to make the scope of the present invention dependent upon such theory, proof, or finding.

What is claimed is:

1. A method of treating a patient to modify a vascular vessel having a defect, the method comprising:
   accessing a treatment site proximate to a defect in a vascular vessel; and
   introducing a remodelable biomaterial into a vessel wall or externally of a vessel wall at the treatment site;
   wherein the remodelable biomaterial is effective to shrink as a result of remodeling so as to reshape the vascular vessel.

2. The method of claim 1 wherein the defect is an aneurysm.

3. The method of claim 1 wherein said accessing comprises inserting a cannulated delivery device intra-lumenally through the vascular vessel.

4. The method of claim 1 wherein said remodelable biomaterial is angiogenic.

5. The method of claim 3 wherein said introducing comprises injecting the remodelable biomaterial through the cannulated delivery device into the vessel wall.

6. The method of claim 3 comprising extending the cannulated delivery device through the vessel wall adjacent the treatment site to deliver the remodelable biomaterial to an external surface of the vessel wall.

7. The method of claim 1 wherein said accessing comprises inserting a cannulated delivery device exo-lumenally to the treatment site.

8. The method of claim 7 comprising injecting the remodelable biomaterial through the cannulated delivery device into the vessel wall.

9. The method of claim 7 comprising delivering the remodelable biomaterial to an external surface of the vessel wall.

10. The method of claim 1 comprising injecting the remodelable biomaterial into two or more sites spaced circumferentially about the vascular vessel.

11. The method of claim 1 wherein said introducing comprises wrapping a sheet of the remodelable biomaterial in contact with the external connective tissue of the vascular vessel.

12. The method of claim 11 wherein the remodelable biomaterial is a laminate comprising two or more sheets of a collagenous material.

13. The method of claim 11 comprising attaching the sheet of remodelable biomaterial to itself to form a band about the external connective tissue of the vascular vessel.

14. The method of claim 1 wherein said introducing comprises delivering an effective amount of the remodelable biomaterial externally of the vascular vessel to reinforce the vascular vessel wall.

15. The method of claim 1 wherein the remodelable biomaterial is a laminate comprising two or more sheets of a collagenous material.

16. The method of claim 1 wherein the remodelable biomaterial comprises an extracellular matrix material.

17. The method of claim 1 wherein the remodelable biomaterial comprises submucosa tissue.

18. The method of claim 1 wherein the remodelable biomaterial comprises collagen.

19. The method of claim 17, wherein said submucosa is porcine, bovine, or ovine submucosa.

20. The method of claim 1 wherein the remodelable biomaterial comprises a bioactive substance.

21. The method of claim 1 wherein the remodelable biomaterial comprises a population of viable cells.

22. The method of claim 21 wherein the cells comprise autologous cells.

23. A method of treating a patient with a vascular defect, said method comprising:
   introducing a delivery device through the patient's vasculature to a treatment site proximate to the vascular defect; and
   delivering a remodelable biomaterial into or externally of a wall of the vessel at the treatment site;
   wherein the remodelable biomaterial is effective to shrink as a result of remodeling so as to reshape the vascular vessel.

24. The method of claim 23 wherein the defect is an aneurysm.

25. The method of claim 23 wherein the defect is a fistula.

26. The method of claim 23 wherein said introducing comprises introducing a delivery device through a vein.

27. The method of claim 23 wherein said introducing comprises introducing a delivery device through an artery.

28. The method of claim 23 wherein said introducing comprises injecting the remodelable biomaterial through the delivery device into the vessel wall.

29. The method of claim 23 comprising extending the delivery device through the vessel wall to deliver the remodelable biomaterial to an external surface of the vessel wall.

30. The method of claim 23 wherein said delivering comprises delivering an effective amount of the remodelable biomaterial externally of the vascular vessel to reinforce the vascular vessel wall.

31. The method of claim 23 wherein the remodelable biomaterial comprises an extracellular matrix material.

32. The method of claim 23 wherein the remodelable biomaterial comprises submucosa tissue.

33. The method of claim 23 wherein the remodelable biomaterial comprises collagen.

34. The method of claim 33, wherein said submucosa is porcine, bovine, or ovine submucosa.

35. The method of claim 23 wherein the remodelable biomaterial comprises a bioactive substance.

36. The method of claim 23 wherein the remodelable biomaterial comprises a population of viable cells.

37. The method of claim 36 wherein the cells comprise autologous cells.

38. A method for treating a vascular vessel in a patient comprising introducing a remodelable biomaterial into or externally of a wall of the vessel in a region proximate to an aneurysm or other wall defect, wherein the remodelable biomaterial is effective to shrink as a result of remodeling so as to reshape the vascular vessel.

39. The method of claim 38 wherein said remodelable biomaterial has a flowable state, and said introducing comprises injecting the remodelable biomaterial while in said flowable state.

40. The method of claim 39 wherein the remodelable biomaterial also has a hardened state, and wherein said method also comprises allowing or causing the remodelable biomaterial to change from said flowable state to said hardened state after said injecting.

41. The method of claim 40 wherein said remodelable biomaterial is effective to be thermally induced to change from said flowable state to said hardened state.

42. The method of claim 39 comprising injecting the remodelable biomaterial into two or more sites spaced circumferentially about the vascular vessel.

43. The method of claim 39 wherein said injecting comprises injecting the remodelable biomaterial so as to substantially surround the vascular vessel.

44. The method of claim 38 wherein the remodelable biomaterial comprises a fluidized extracellular matrix material.

45. The method of claim 38 wherein the remodelable biomaterial comprises at least one extracellular matrix material selected from the group consisting of pericardium, submucosa, liver basement membrane, dura mater, peritoneum, serosa, and renal capsule.

46. The method of claim 38, also comprising introducing a population of viable cells with the remodelable biomaterial.

47. The method of claim 46 wherein the cells comprise autologous cells.

48. The method of claim 38 wherein the remodelable biomaterial comprises a bioactive agent.

49. The method of claim 38 wherein said introducing an amount of the remodelable biomaterial sufficient to reinforce the vessel wall.

* * * * *